United States Patent
Yeon et al.

(10) Patent No.: US 8,643,377 B2
(45) Date of Patent: Feb. 4, 2014

(54) METHOD OF DETECTING IMPURITIES IN HIGH TEMPERATURE AQUEOUS SOLUTION AND APPARATUS OF DETECTING IMPURITIES FOR THE SAME

(75) Inventors: Jei-Won Yeon, Daejeon (KR); Kyuseok Song, Daejeon (KR); Jaesik Hwang, Daejeon (KR); Myung Hee Yun, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 466 days.

(21) Appl. No.: 12/962,805

(22) Filed: Dec. 8, 2010

(65) Prior Publication Data

US 2012/0081133 A1 Apr. 5, 2012

(30) Foreign Application Priority Data

Sep. 30, 2010 (KR) .................. 10-2010-0095442

(51) Int. Cl.
*G01N 27/02* (2006.01)
*G01R 27/08* (2006.01)
*G01N 27/26* (2006.01)

(52) U.S. Cl.
USPC ............................ 324/439; 324/693; 204/400

(58) Field of Classification Search
USPC ......... 324/693, 691, 649, 600, 713, 348, 425, 324/439, 444; 73/31.02, 31.03; 204/193, 204/194, 400
See application file for complete search history.

(56) References Cited

U.S. PATENT DOCUMENTS

| | | | |
|---|---|---|---|
| 4,028,197 A * | 6/1977 | Capuano .................. | 205/780 |
| 4,699,718 A | 10/1987 | Jones et al. | |
| 4,831,324 A * | 5/1989 | Asakura et al. .......... | 324/615 |
| 4,863,571 A * | 9/1989 | Chambaere ............... | 205/776.5 |
| 5,448,178 A * | 9/1995 | Chen et al. ............... | 205/775.5 |
| 7,033,481 B1 * | 4/2006 | Schlager et al. .......... | 205/701 |
| 2008/0116908 A1 * | 5/2008 | Potyrailo et al. ......... | 324/721 |
| 2008/0283395 A1 * | 11/2008 | Rhee et al. ............... | 204/400 |

FOREIGN PATENT DOCUMENTS

| | | |
|---|---|---|
| KR | 1019940040300 A | 4/1998 |
| KR | 1019990044562 A | 5/2001 |
| KR | 1020110024893 A | 3/2011 |

* cited by examiner

*Primary Examiner* — Hoai-An D Nguyen
(74) *Attorney, Agent, or Firm* — Maier & Maier, PLLC (57) ABSTRACT

A method of detecting impurities in a high-temperature aqueous solution and an apparatus of detecting impurities for the same. Specifically, the present invention provides a method of detecting impurities in a high-temperature aqueous solution comprising a reducing agent using an electrochemical water chemistry technology detecting the electrochemical current varied according to the degree in which the impurities in the high-temperature aqueous solution hinder the formation of an oxide film that is formed on a noble metal electrode, and an impurity detecting apparatus comprising a noble metal electrode, a counter electrode, and a device of applying the electrochemical potential and measuring the electrochemical current for the method of detecting impurities.

12 Claims, 9 Drawing Sheets

METHOD OF DETECTING IMPURITIES IN HIGH TEMPERATURE AQUEOUS SOLUTION AND APPARATUS OF DETECTING IMPURITIES FOR THE SAME

CROSS-REFERENCES TO RELATED APPLICATION

This patent application claims the benefit of priority from Korean Patent Application No. 10-2010-0095442, filed on Sep. 30, 2010, the contents of which are incorporated herein by reference.

BACKGROUND OF THE INVENTION

1. Field of the Invention

The present disclosure relates to a method of detecting impurities in a high-temperature aqueous solution and an apparatus of detecting impurities for the same.

2. Description of the Related Art

It has been known that one of principal causes of damages or failures of pressure vessels, heat exchange pipes, water supply pipes and turbines that are important in wholesomeness and economic feasibility of high temperature energy systems such as nuclear power plants or thermoelectric power plants comes from corrosion phenomena generated by cooling water at high temperatures and high pressures. A dissociation constant of water is increased, and an activity of chemical species causing the corrosion is also increased at high temperatures to accelerate corrosion of metals. Accordingly, metallic structure material brought into contact with high-temperature cooling water is exposed to a high corrosion environment. Therefore, stainless steel or special alloy with high corrosion resistance is generally used as the metallic structure material. However, even although the above-mentioned stainless steel with high corrosion resistance is used, there is a problem that local corrosion such as pitting is progressed even in an alloy such as stainless steel in an environment with highly corrosive chemical species such as chloride ions. Therefore, limitation values of the concentration for such chemical species causing corrosion are being strictly controlled. However, a method of detecting harmful chemical species including anionic chemical species such as chloride ions in real-time without sampling in the state of high-temperature cooling water has not been developed yet.

Currently, conventional analysis methods for detecting chloride ions may include an ion chromatography method and a method of using an ion-selective electrode. A technology of simultaneously measuring boric acid and chloride ions of cooling water in a nuclear power plant by an ion chromatography method is reported in U.S. Pat. No. 4,699,718. Additionally, Passell has developed a system of monitoring quality of cooling water using an on-line chromatography (J. Chromatography A, 671 (1-2), pp. 331-337, 1994), and Reden, et al. have reported a method of measuring the anions in real-time using a chromatography system which is capable of measuring anions through on-line (Faelleskemikerne, Power plant chemical technology, Denmark, 1996. P. 14.1-14.15).

Furthermore, Moskvin, et al. has reported a method of measuring in real-time the concentration of chloride ions in cooling water using an ion-selective electrode (Atomnaya Ehnergiya, USSR. March 1975. V. 38(3) p. 143-145), and Sekeka, et al. has also reported a method of measuring the concentration of chloride ions up to a concentration range of 0.05 to 3.5 ppm in cooling water of heavy-water reactor (CANDU) type nuclear power plant using an ion-selective electrode (J. the Association of Official Analytical Chemists, USA. May 1977. V. 60(3) p. 625-627). Florence has also reported on a technology of measuring the concentration of chloride ions using an ion-selective electrode (J. Electroanalytical Chemistry, 31 (1), pp. 77-86, 1971). However, the foregoing conventional methods are methods that are capable of being applied only in room temperature, and have a limitation that they cannot be applied to an aqueous solution at high temperatures.

On the other hand, Korean Patent Laid-open Publication No. 2009-0083073 has reported a method of detecting the existence of chloride ions using a platinum electrode at high temperatures. However, the foregoing method is based on a technology of measuring a difference in oxidation currents of dissolved hydrogen under the steady state simply when passing dissolved hydrogen through the noble metal oxide film with different porosities by using a porosity difference of noble metal oxide films formed according to the concentration of chloride ions. Therefore, the foregoing method has a limitation that there is a difficulty in detecting chloride ions of low concentration although the method is capable of being applied to high temperature conditions of an aqueous solution.

Thus, the present inventors have developed an original technology capable of measuring the concentration of chloride ions from a transition that oxidation current decreases according to application time of electrochemical potential based on the fact that growth rate of a platinum oxide film is influenced by the concentration of chloride ions when the platinum oxide film is moved by an electrochemical potential produced instead of the oxidation current difference under the steady state by using an electrode of noble metal such as platinum, thereby leading to completion of the present invention.

SUMMARY OF THE INVENTION

An object of the present invention is to provide a method of detecting impurities in a high-temperature aqueous solution and an apparatus of detecting impurities for the same.

In order to achieve the object, the present invention provides a method of detecting impurities in a high-temperature aqueous solution comprising a reducing agent using an electrochemical water chemistry technology. This technology is detecting the electrochemical current varied according to the degree in which the impurities in the high-temperature aqueous solution hinder the formation of an oxide film that is formed on a noble metal electrode, and an impurity detecting apparatus comprising a noble metal electrode, a counter electrode, and a device of applying the electrochemical potential and measuring the electrochemical current for the method of detecting impurities.

A method of detecting impurities in a high-temperature aqueous solution and an apparatus of detecting impurities for the same have effects in that they are capable of being usefully used for detecting the inflow of impurities in an aqueous solution used at high temperatures by using a phenomenon that the formation rate of an oxide film on the surface of noble metal is retarded in the case that impure ions such as chloride ions exist. The method is also based on the phenomenon that electrochemical reactions such as oxidation reactions of dissolved hydrogen are inhibited in a potential region in which an oxide film is stabilized on noble metal such as platinum in the high-temperature aqueous solution. The measurement of the current change generated when the potential of the noble metal electrode is shifted to the potential forming a stable oxide film, thereby is serving the function of detecting the concentration of chloride ions flown into the high-temperature aqueous solution.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides a method of detecting impurities in a high-temperature aqueous solution comprising a reducing agent using an electrochemical water chemistry technology detecting the electrochemical current varied according to the degree in which the impurities in the high-temperature aqueous solution hinder the formation of an oxide film that is formed on a noble metal electrode.

A method of detecting impurities in a high-temperature aqueous solution according to the present invention is a detecting method capable of detecting a change in the corresponding current according to the degree in which the impurities in the high-temperature aqueous solution hinder the formation of an oxide film on a noble metal electrode, and grasping the concentration of impurities through the detected change in the corresponding current.

Room-temperature Electrochemical behavior of lithium borated water in which dissolved hydrogen is generally existed is relatively simple and well-known (J.-W. Yeon, J Appl Electrochem (2007) 37:905-912). The room-temperature Electrochemical behavior shows typical electrochemical characteristics that water is reduced to generate hydrogen gas if a reduction potential is applied, and water is oxidized into oxygen gas if a higher oxidation potential is applied rather than that dissolved hydrogen is oxidized if an oxidation potential is applied, based on an open circuit potential ($E_{OCP}$).

Figure 1:
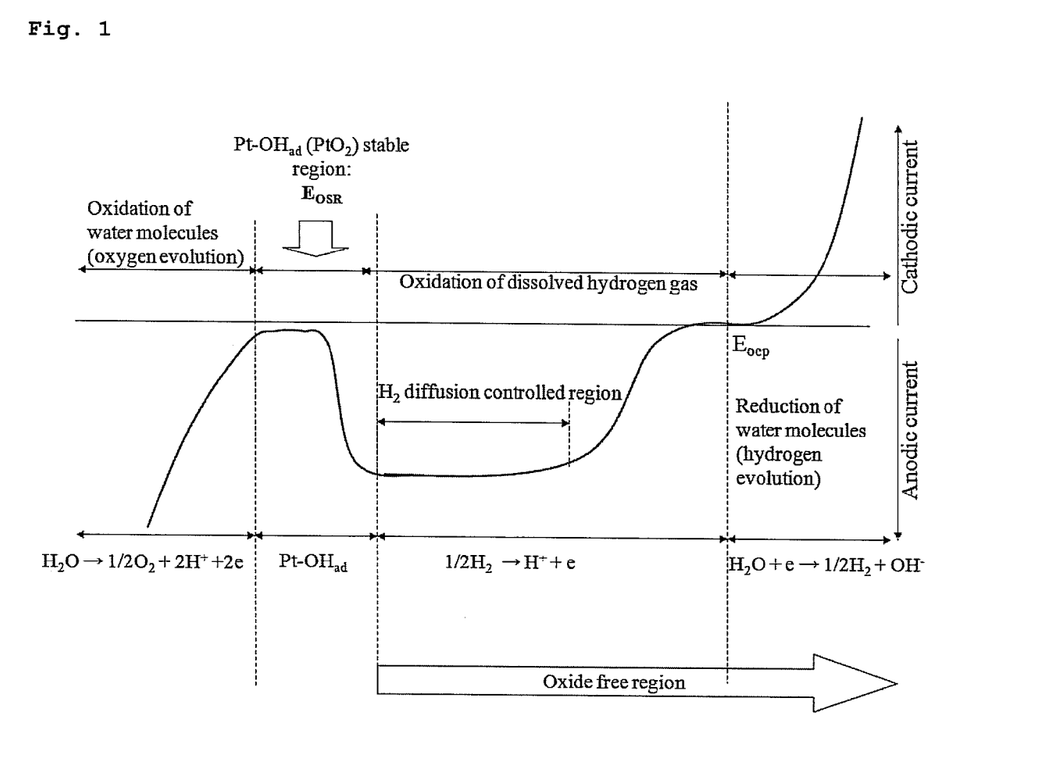
FIG. 1 is a conceptual view in which electrochemical polarization characteristics of a platinum (Pt) electrode are described with the reaction being focused in a high-temperature aqueous solution in which dissolved hydrogen exists.

However, there are general characteristics that, as the temperature increases, the diffusion rate of chemical species in an aqueous solution increases, and the reaction activation energy decreases such that the electrochemical reaction rate rapidly increases according to an increase in temperature. Electrochemical behavior of noble metal electrode shows a peculiar behavior different from general electrochemical behavior in the high-temperature aqueous solution in which dissolved hydrogen exists, which is illustrated as a graph of FIG. 1.

Figure 2:
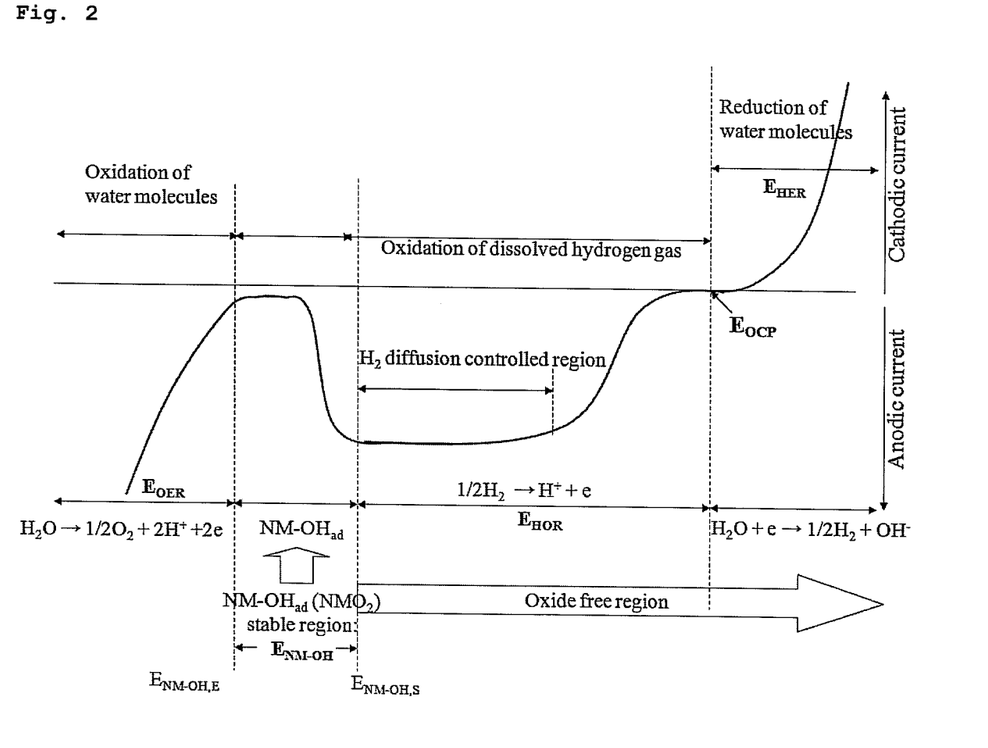
FIG. 2 is a conceptual view in which electrochemical polarization characteristics of a noble metal electrode are described along with the principal electrochemical potential in a high-temperature aqueous solution in which dissolved hydrogen exists.

On the other hand, at high temperatures, current magnitude increases as much as at least about 50 times in the entire potential region compared to room temperature, and a hydrogen gas-generating region, a dissolved hydrogen-oxidizing region, and an oxygen gas-generating region exist as in the room temperature. However, if the oxidation potential is applied at high temperatures, the oxidation reaction of dissolved hydrogen occurs, and a potential region is generated in which oxidation current different from that of room temperature is dominated by diffusion of dissolved hydrogen at a predetermined potential or more. Furthermore, there is a particularity that there exists a potential region ($E_{pt\text{-}OH}$) in which an electrochemical potential decreases suddenly if a further higher oxidation potential is applied at high temperatures. This is due to the reason that a stable oxide film is formed on the surface of a noble metal electrode. Although a potential region in which the oxide film is stable exists irrespective of temperature values, there are characteristics that an oxidation reaction rate greatly decreases since the electrode reaction rate is very high at high temperatures differently from room temperature such that a reaction-inhibiting influence of oxide film is acted relatively largely on the potential region where the oxide film exists. Electrochemical polarization characteristics of a noble metal electrode in a high-temperature aqueous solution in which dissolved hydrogen exists are illustrated in FIG. 2 through a graph together with an electrochemical potential.

Although it varies according to an exposed environment, an oxide film is formed on the surface of a noble metal electrode within about 0.5 second when applying an electrochemical potential to a region where the oxide film is stable from a region where the oxide film does not exist on the noble metal electrode using the peculiar electrochemical behavior of a noble metal electrode in the high-temperature aqueous solution in which dissolved hydrogen exists, wherein there are characteristics that the electrochemical reaction such as the oxidation reaction of dissolved hydrogen is suppressed in the potential region where the oxide film exists stably.

After completing the formation of the oxide film on the surface of the noble metal electrode, the oxidation reaction of dissolved hydrogen is suppressed by the formed oxide film such that the oxidation reaction rate is greatly dropped. Furthermore, although the steady-state oxidation reaction rate of dissolved hydrogen is influenced by a porosity difference of the oxide film if impurities such as chloride ions are existed in a large amount, the oxidation reaction rate of dissolved hydrogen is not greatly influenced by a trace of chloride ions.

Figure 3:
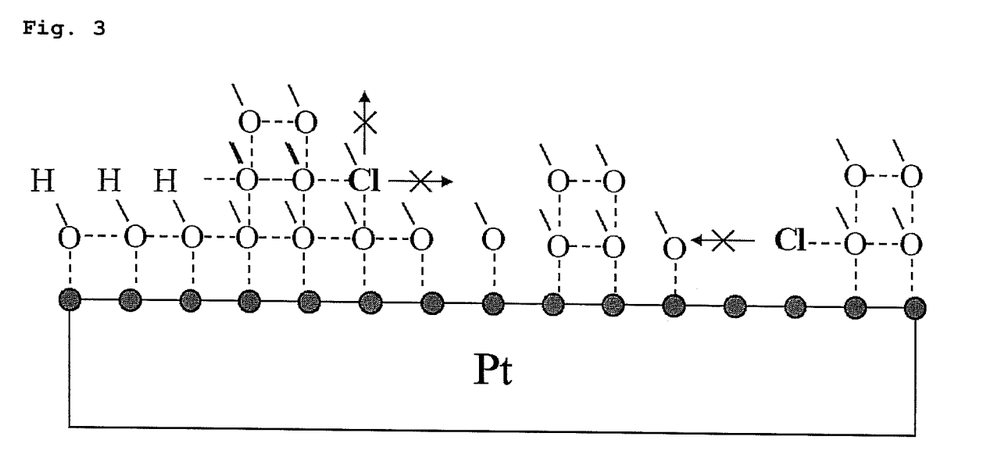
FIG. 3 is a conceptual view showing an action that chloride ions hinder the formation of a platinum oxide film in a potential region in which a platinum oxide film is formed.

However, for instance, chloride ions of monovalent are known to be chemical species in which mono-valent chloride ions are bonded to bivalent oxygen atoms on the metal surface to lower the formation rate of a metal oxide film by dropping a reaction in which oxygen and oxygen are continuously bonded to each other as illustrated in FIG. 3. Therefore, although a trace of chloride ions is not capable of influencing the formation of an oxide film after completing the formation of the oxide film on the surface of the noble metal electrode, there is a great drop in the formation of the oxide film even in the trace amount of the chloride ions during a short period of oxide film-forming time when instantaneously moving an electrochemical potential to a potential region in which the oxide film is stable from a potential region in which there is not the oxide film on the surface of noble metal electrode. Therefore, chloride ions delay the formation of the oxide film on the surface of the noble metal electrode, and a phenomenon that oxidation current of dissolved hydrogen is reduced is also delayed by chloride ions accordingly.

Figure 4:
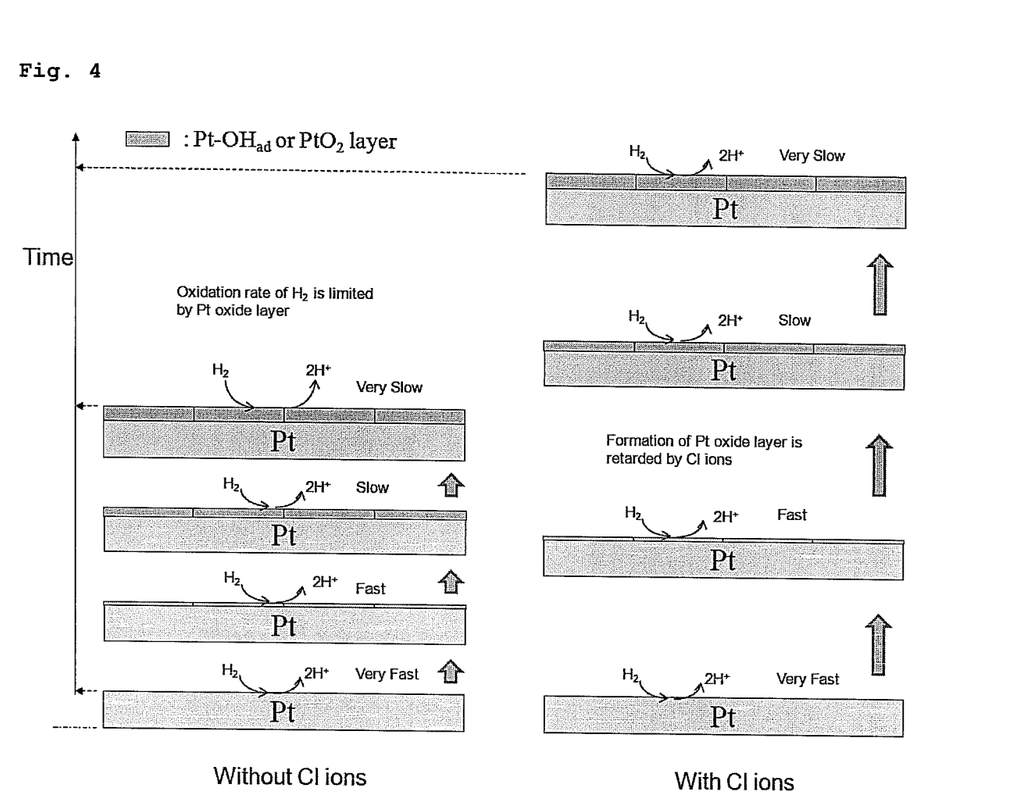
FIG. 4 is a conceptual view illustrating, according to time, an influence of chloride ions on the oxidation reaction of dissolved hydrogen and an action that chloride ions hinder the formation of a platinum oxide film in a potential region in which the platinum oxide film is formed.

Meanwhile, the more the concentration of chloride ions increases, the more or the longer the oxidation reaction current of dissolved hydrogen observed when applying an electrochemical potential in which the oxide film is stable lasts. The concentration of chloride ions can be calculated from the magnitude of oxidation current measured using a relationship between the concentration of chloride ions and oxidation reaction current of dissolved hydrogen. Chloride ions delay the formation of the oxide film on the surface of the noble metal electrode, and a relation in which the oxidation reaction current of dissolved hydrogen continues is illustrated through a conceptual view of FIG. 4 accordingly.

Figure 5:
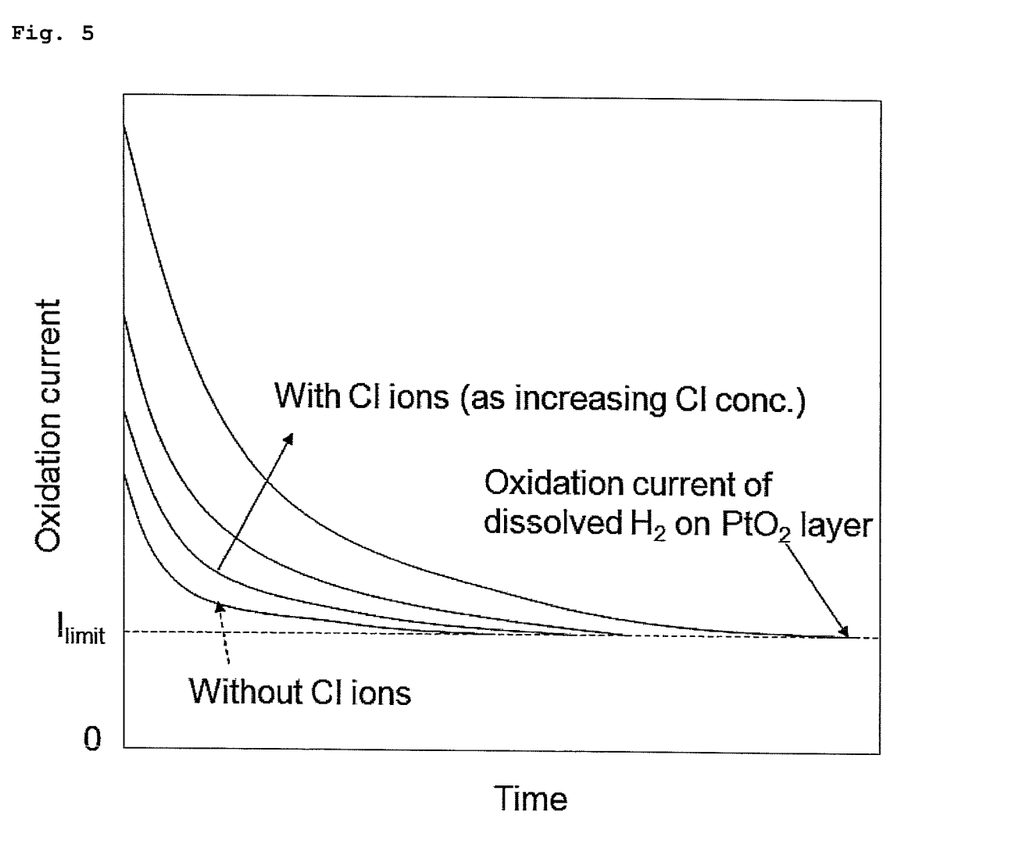
FIG. 5 is a graph showing a phenomenon in which a decrease in oxidation current is suppressed according to the concentration of chloride ions in a potential region in which a platinum oxide film is formed.

Furthermore, the rate in which dissolved hydrogen is oxidized through the oxide film depending on the degree which the oxide film is formed on the surface of the noble metal electrode is exponentially changed. For instance, if the concentration of chloride ions that are impurities increases, the formation of the oxide film deteriorates by chloride ions such that the oxidation reaction current of dissolved hydrogen tends to last for a long time, and the concentration of chloride ions that are impurities can be calculated by a change in the oxidation reaction current of dissolved hydrogen reduced during a period of time when the oxide film is formed. It is illustrated through a graph in FIG. 5 that the oxidation reaction current of dissolved hydrogen is changed depending on the concentration of chloride ions that are impurities.

As described above, the present invention has characteristics that are capable of measuring a change in the oxidation reaction current of dissolved hydrogen depending on the degree which the oxide film is formed on the surface of the noble metal electrode, and that are capable of measuring the concentration of impurities through the change in the oxidation reaction current of dissolved hydrogen, and the present invention has an effect of measuring the concentration of impurities in real-time.

On the other hand, a noble metal electrode of the present invention is preferably one selected from the group consisting of platinum (Pt), gold (Au), rhenium (Re), ruthenium (Ru), rhodium (Rh), palladium (Pd) and iridium (Ir) which are chemically stable in a high-temperature aqueous solution, and in which formation and reduction of the oxide film are reversibly generated, or alloys thereof, the noble metal electrode of the present invention is more preferably one selected from the group consisting of platinum (Pt), gold (Au) and palladium (Pd), or alloys thereof, and the noble metal electrode of the present invention is most preferably platinum (Pt) or an alloy thereof.

Furthermore, the reducing agent existing in the high-temperature aqueous solution is preferably one selected from the group consisting of dissolved hydrogen, ammonia and hydrazine ($N_2H_4$), or mixtures thereof. All of the foregoing materials are materials capable of generating dissolved hydrogen in the high-temperature aqueous solution, and the oxidation reaction of dissolved hydrogen can be induced through the materials.

Furthermore, dissolved hydrogen in the aqueous solution generated by the reducing agent preferably has a concentration range of 1 cc $H_2$/kg to 200 cc $H_2$/kg.

In the case that dissolved hydrogen in the aqueous solution has a concentration of less than 1 cc $H_2$/kg, there is a problem that it is difficult to detect the growth of an oxide film on a noble metal electrode, thereby making it difficult to measure impure ions since it is not possible to sufficiently obtain an oxidation reaction current of dissolved hydrogen. In the case that dissolved hydrogen has a concentration of more than 200 cc $H_2$/kg, there are problems in management of high-temperature cooling water as well as measurement of impure ions such as hydrogen embrittlement of nuclear fuel cladding material, acceleration of Crud deposition according to an increase in solubility of metal oxides, and safety during cooling and opening of cooling water.

Furthermore, a high-temperature aqueous solution of the present invention preferably has a temperature of 80° to 375° C.

There is a problem that electrochemical behavior is not exhibited clearly at high temperatures differently from room temperature if the high-temperature aqueous solution has a temperature less than 80° C. while there is a problem that electrochemical measurement is not smoothly made due to a low electric conductivity at a temperature of the aqueous solution exceeding 375° C. since hydrogen bond of water is broken at the temperature such that water is converted into supercritical water that is a nonpolar solvent.

Meanwhile, a reduction potential region applied to the noble metal electrode preferably has a potential region lower (or more cathodic) than an adsorbed hydroxyl-stabilizing potential ($E_{NM-OH,S}$) of the noble metal electrode. Furthermore, the reduction potential region preferably comprises an open circuit potential ($E_{OCP}$) of the noble metal electrode.

The reason for this is that an electrochemical potential of the noble metal electrode for the detecting method of the present invention should be moved from the reduction potential region to the oxidation potential region, and the electrochemical potential should be applied to the oxidation potential region in which the oxide film is formed in a state that the oxide film is not formed on the surface of the noble metal electrode. Therefore, it is preferable to have a potential region at the side of the reduction potential region, i.e., lower (or more cathodic) than an electrochemical potential in which the oxide film is stably formed on the noble metal electrode as in the foregoing range. Furthermore, the reduction potential region preferably comprises an open circuit potential ($E_{OCP}$) of the noble metal electrode.

An oxidation potential region applied to the noble metal electrode preferably has a potential region higher (more anodic) than an adsorbed hydroxyl-stabilizing potential ($E_{NM-OH,S}$) of the noble metal electrode.

Furthermore, the oxidation potential region preferably has a potential region which is higher (more anodic) than the adsorbed hydroxyl-stabilizing potential ($E_{NM-OH,S}$) of the noble metal electrode and lower (more cathodic) than an oxygen generation-starting potential ($E_{NM-OH,E}$). The reason for this is that an oxide film is stably formed on the noble metal electrode in the potential region which is higher (more anodic) than the adsorbed hydroxyl-stabilizing potential ($E_{NM-OH,S}$) and lower (more cathodic) than the oxygen generation-starting potential ($E_{NM-OH,E}$).

Furthermore, it is preferable to limit to the oxidation potential region more than the hydrogen gas-generating potential region and limit to the reduction potential region more than the oxygen gas-generating potential region since it is preferable that the oxidation potential region or the reduction potential region applied to the noble metal electrode avoids the hydrogen gas generating potential region or oxygen gas generating potential region respectively.

Therefore, it is most preferable to set an open circuit potential ($E_{OCP}$) of the noble metal electrode with the reduction potential and set $E_{NM-OH,M}$ (a mean potential between $E_{NM-OH,S}$ and $E_{NM-OH,S}$) with the oxidation potential in the impurity detecting method of the present invention.

On the other hand, the detecting method of the present invention comprises performing the movement of an electrochemical potential from the reduction potential to the oxidation potential sequentially and repetitiously in order to detect impurities successively. On noble metal such as platinum, the formation of an oxide film and the reduction of the oxide film are performed very fast at rates that are almost similar to each other. Therefore, the oxide film is formed within about 0.1 second when there are no impurities while the oxide film is formed within about 0.5 second even when the impurities exist. Furthermore, the oxide film formed by the application of the reduction potential during the similar period of time is reduced. That is, the detecting method of the present invention is capable of performing the processes of oxidation and reduction for 0.2 second to less than 1 second depending on the concentration of impurities in the high-temperature aqueous solution.

Therefore, the noble metal electrode preferably has a reduction potential and an oxidation potential sequentially applied thereto at time intervals exceeding 0.2 second. The noble metal electrode more preferably has a reduction potential and an oxidation potential sequentially applied thereto at time intervals exceeding 1 second.

Figure 6:
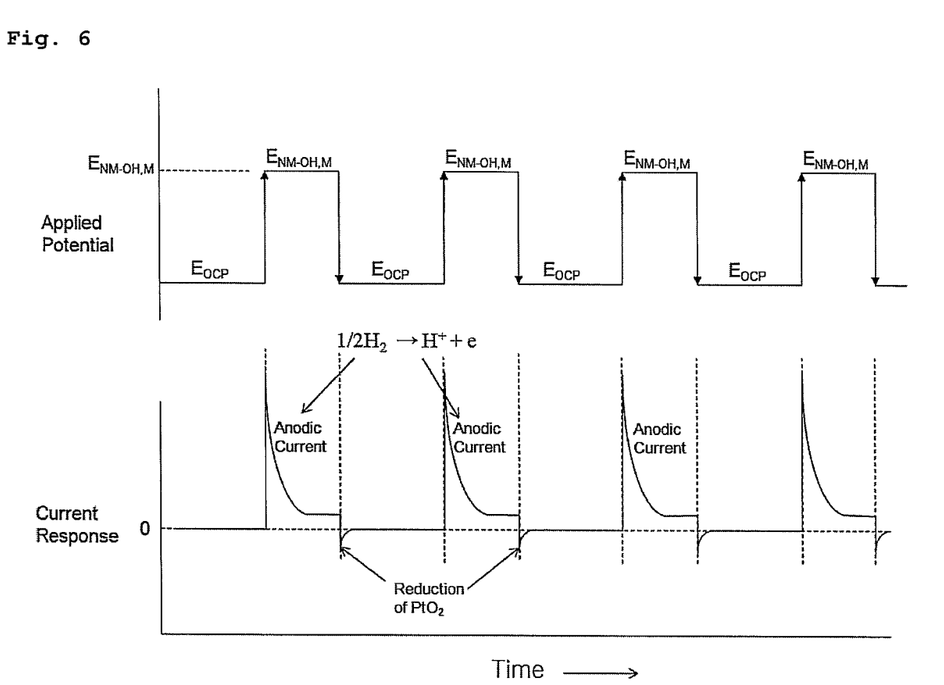
FIG. 6 is a graph showing that an electrochemical potential is repetitiously applied to the platinum electrode for successively measuring the concentration of chloride ions.

FIG. 6 illustrates a repetitive potential-applying method capable of successively measuring the concentration of chloride ions as impurities using a noble metal electrode as a work electrode and a typical example of electrochemical current caused by the potential application.

The impurities capable of being detected in the detecting method of the present invention comprise halogen ions inhibiting the formation of a metal oxide film. Preferably, chloride ions (Cl$^-$) most inhibiting the formation of a metal oxide film are detected as the impurities by the detecting method of the present invention.

It is preferable to control the concentration by detecting the concentration of the impurities by the detecting method of the present invention since the halogen ions carry out a role of inhibiting the formation of the oxide film formed on the noble metal electrode, and the chloride ions cause metal corrosion in an aqueous solution with dissolved hydrogen such as cooling water in a nuclear power plant.

Figure 7:
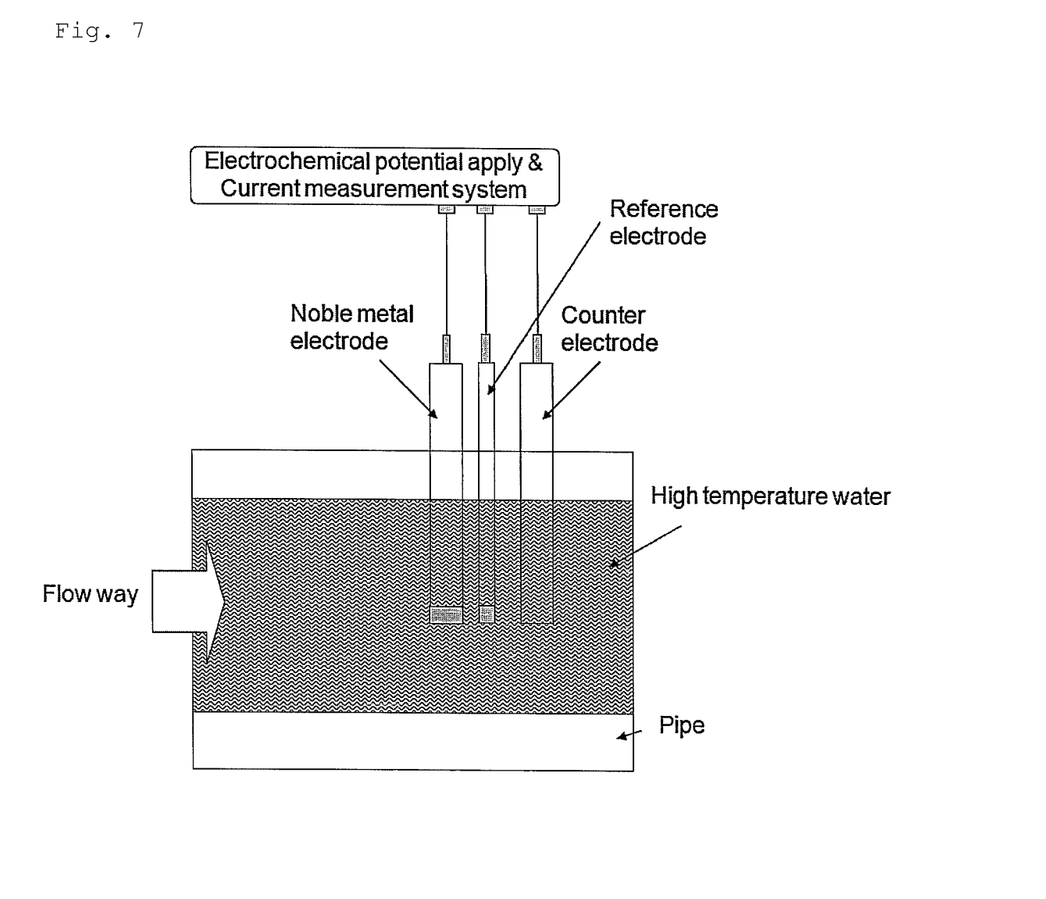
FIG. 7 is a conceptual view showing an example of a possible measuring apparatus of the present invention using an electrochemical water chemistry technology.

On the other hand, the present invention provides an impurity detecting apparatus for the impurity detecting method comprising: a noble metal electrode; a counter electrode; and a device of applying the electrochemical potential and measuring the electrochemical current, and a conceptual view of the impurity detecting apparatus is illustrated in FIG. 7. It is preferable that the noble metal electrode is one selected from the group consisting of platinum (Pt), gold (Au), rhenium (Re), ruthenium (Ru), rhodium (Rh), palladium (Pd) and iridium (Ir), or alloys thereof.

It is more preferable that the noble metal electrode is one selected from the group consisting of platinum (Pt), gold (Au) and palladium (Pd), or alloys thereof.

It is most preferable that the noble metal electrode is platinum (Pt) or an alloy thereof.

The reason for this is that the metals are chemically stable in the high-temperature aqueous solution, and formation and reduction of the oxide film are reversibly repeated.

Furthermore, the noble metal electrode should be floating grounded since a pipe on which the apparatus is generally installed should be grounded.

Furthermore, the counter electrode is preferably metal or conductive nonmetal, and a structural material itself brought into contact with a high-temperature aqueous solution to simplify a measuring system is capable of being applied as the counter electrode.

Furthermore, the impurity detecting apparatus may further comprise a reference electrode.

The reference electrode is a part that can be removed when a potential-current relationship between the noble metal electrode and counter electrode is confirmed. The reference electrode can be removed to simplify the measuring system.

Hereinafter, the present invention will be described in more detail with reference to the following experimental example. However, the following experimental example is provided for illustrative purposes only, and the scope of the present invention should not be limited thereto in any manner.

EXPERIMENTAL EXAMPLE 1

Measuring the Concentration of Chloride Ions

A current change was measured by using a counter electrode along the concentration (0~100 ppm) of chloride ions when moving a platinum electrode having an exposure area of 1.0 cm$^2$ from an open circuit potential ($E_{OCP}$) of the platinum electrode having $-0.65\pm0.05$ $V_{Ag/AgCl}$ to a platinum oxide film-stabilizing potential ($E_{PT-OH,M}$) having +0.5 $V_{Ag/AgCl}$ in a lithium borate aqueous solution having a high temperature (280° C.) in which chloride ions existed.

Figure 8:
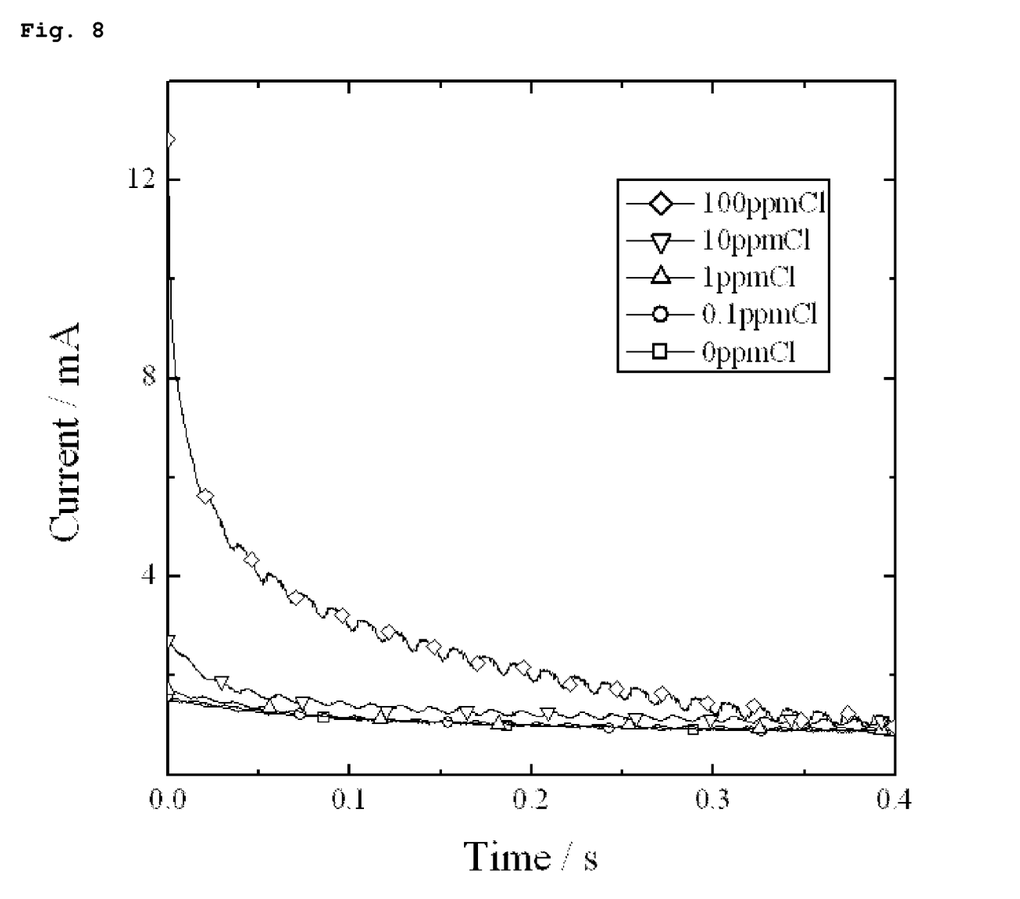
FIG. 8 is a graph showing a change in currents measured in Experiment example 1 of the present invention.

FIG. 8 illustrates a graph in which oxidation current of dissolved hydrogen is measured during a period of time in which the platinum oxide film is formed on the surface of the platinum electrode when applying +0.5 $V_{Ag/AgCl}$ to the platinum electrode in the lithium borate aqueous solution having a high temperature (280° C.) in which chloride ions exist. As illustrated in FIG. 8, it can be seen that the more the concentration of chloride ions increases, the more the initial current value increases, and the formation of the oxide film is completed to delay the time that is taken for the concentration of chloride ions to reach a predetermined oxidation current value. Furthermore, it can be seen that all concentration values of chloride ions reach the predetermined oxidation current value of 1 mA cm$^{-1}$ after about 0.4 second in the entire concentration range including a case that the concentration of chloride ions is 100 ppm.

Figure 9:
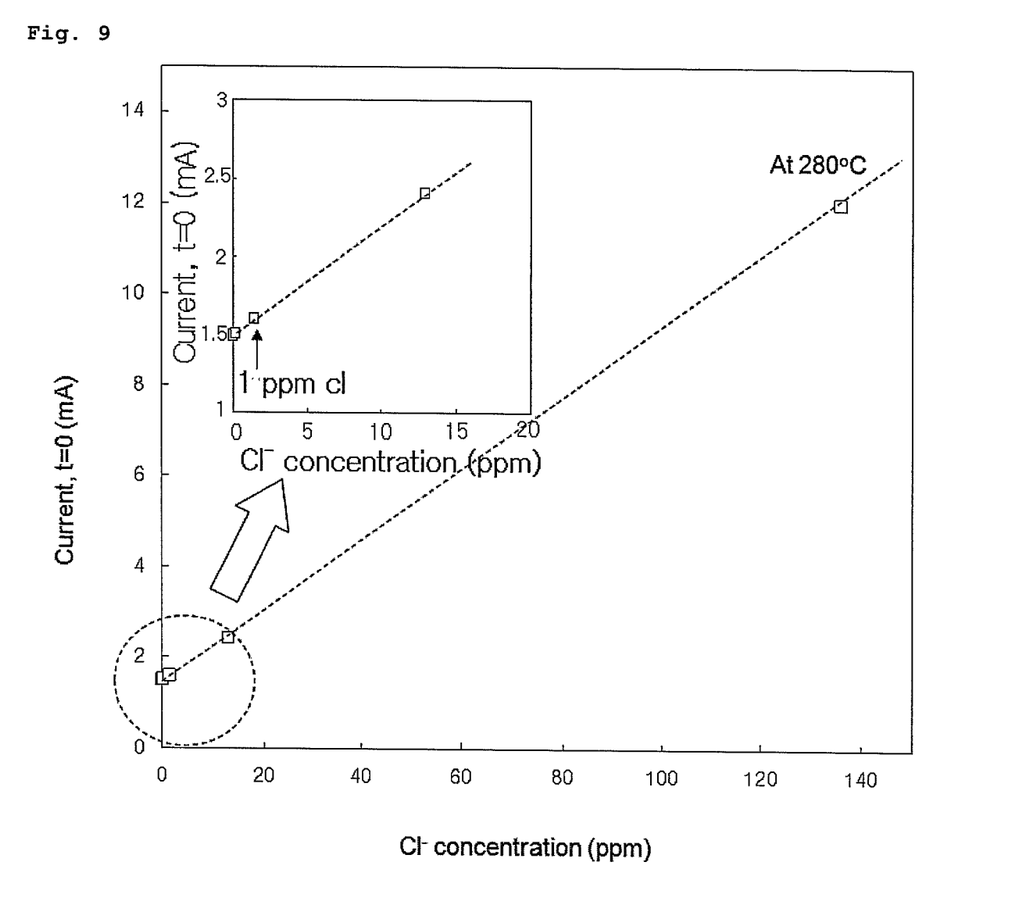
FIG. 9 is a graph showing a relationship between the concentration of chloride ions and the initial oxidation current value on applying the electrochemical potential in Experiment example 1 of the present invention.

Furthermore, FIG. 9 is a graph in which the concentration of chloride ions is illustrated from maximum current values ($I_{t=0}$) in which oxidation currents of dissolved hydrogen are measured during a period of time while a platinum oxide film is formed on the surface of the platinum electrode. As illustrated in FIG. 9, it can be seen that a small amount of chloride ions of about 1 ppm can be clearly detected by the detecting method of the present invention.

As shown in FIG. 8 and FIG. 9, it can be seen that a detecting method of the present invention is capable of clearly detecting chloride ions existing as impurities in a high-temperature aqueous solution by a change in current values measured depending on the concentration of chloride ions, and the detecting method of the present invention is also capable of measuring the concentration of the detected chloride ions. It was confirmed through the detecting method of the present invention that the detecting method of the present invention had effects capable of detecting and measuring the concentration of halogen ions including chloride ions existing as impurities in a high-temperature aqueous solution in real-time, and detecting the chloride ions causing the corrosion of metal in cooling water of a nuclear power plant.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of detecting impurities in a high-temperature aqueous solution comprising a reducing agent using an electrochemical water chemistry technology, the method comprising the following steps of:

dipping a noble metal electrode and a counter electrode in unknown samples comprising impurities therein;

forming an oxide film on the noble metal electrode by moving an electric potential from a reduction potential lower (more cathodic) than an adsorbed hydroxyl-stabilizing potential ($E_{NM-OH,S}$) of the noble metal electrode and higher than an open circuit potential ($E_{OCP}$) of the noble metal electrode to an oxidation potential higher (more anodic) than an adsorbed hydroxyl-stabilizing potential ($E_{NM-OH,S}$) of the noble metal electrode and lower (more cathodic) than an oxygen generation-starting potential($E_{NM-OH,E}$);

obtaining a current value measured in the forming of the oxide film, and obtaining the concentration of the impurities in a high temperature aqueous solution based on the measured current value.

2. The method as set forth in claim 1, wherein the noble metal electrode is one selected from the group consisting of platinum (Pt), gold (Au), rhenium (Re), ruthenium (Ru), rhodium (Rh), palladium (Pd) and iridium (Ir), or alloys thereof.

3. The method as set forth in claim 1, wherein the noble metal electrode is one selected from the group consisting of platinum (Pt), gold (Au) and palladium (Pd), or alloys thereof.

4. The method as set forth in claim 1, wherein the noble metal electrode is platinum (Pt) or an alloy thereof.

5. The method as set forth in claim 1, wherein the reducing agent is one selected from the group consisting of dissolved hydrogen, ammonia and hydrazine ($N_2H_4$), or mixtures thereof.

6. The method as set forth in claim 5, wherein dissolved hydrogen in the aqueous solution generated by the reducing agent has a concentration range of 1 cc $H_2$/kg to 200 cc $H_2$/kg.

7. The method as set forth in claim 1, wherein the high-temperature aqueous solution has a temperature of 80° to 375 ° C.

8. The method as set forth in claim 1, further comprising the following steps of:

obtaining a calibration curve by the method comprising, dipping the noble metal electrode and the counter electrode in known samples, each of which containing the impurities at different concentrations, and forming the oxide film on the noble metal electrode by moving an electric potential from a reduction potential lower (more cathodic) than an adsorbed hydroxyl-stabilizing potential ($E_{NM-OH,S}$) of the noble metal electrode and higher than an open circuit potential ($E_{OCP}$) of the noble metal electrode to an oxidation potential higher (more anodic) than an adsorbed hydroxyl-stabilizing potential ($E_{NM-OH,S}$) of the noble metal electrode and lower (more cathodic) than an oxygen generation-starting potential ($E_{NM-OH,E}$), obtaining the current value measured in the forming of the oxide film, and obtaining a calibration curve based on the current value obtained and concentrations of the impurities in each sample; and obtaining the concentrations of the impurities in the unknown samples by applying the current value obtained from the unknown samples to the calibration curve.

9. The method as set forth in claim 1, wherein the impurities comprise chloride ions (Cl$^-$) most inhibiting the formation of a metal oxide film.

10. The method as set forth in claim 1, wherein the impurities comprise halogen ions inhibiting the formation of a metal oxide film.

11. The method as set forth in claim 1, wherein the noble metal electrode has a reduction potential and an oxidation potential sequentially applied thereto at time intervals exceeding 1 second.

12. The method as set forth in claim 1, wherein the noble metal electrode has a reduction potential and an oxidation potential sequentially applied thereto at time intervals exceeding 0.2 second.

* * * * *